United States Patent [19]

Fues et al.

[11] Patent Number: 5,308,623
[45] Date of Patent: * May 3, 1994

[54] RESORBABLE BONE WAX

[75] Inventors: Johann-Friedrich Fues, Grevenbroich; Wolfgang Ritter, Haan, both of Fed. Rep. of Germany

[73] Assignee: Henkel Kommanditgesellschaft auf Aktien, Dusseldorf, Fed. Rep. of Germany

[*] Notice: The portion of the term of this patent subsequent to Sep. 1, 2009 has been disclaimed.

[21] Appl. No.: 842,823

[22] Filed: Feb. 27, 1992

Related U.S. Application Data

[63] Continuation of Ser. No. 385,138, Jul. 25, 1989, Pat. No. 5,143,730.

[30] Foreign Application Priority Data

Jul. 25, 1988 [DE] Fed. Rep. of Germany ....... 3825211

[51] Int. Cl.$^5$ ........................... A61F 2/28; A61F 2/02
[52] U.S. Cl. .................................. 424/426; 424/78.18; 424/422; 424/423; 424/486; 424/600; 424/617; 424/682; 424/722; 523/113; 523/114; 523/115; 623/16; 623/66
[58] Field of Search ............... 424/426, 422, 423, 486, 424/78.18, 600, 617, 682, 722; 523/114, 115, 113; 623/16, 66

[56] References Cited

U.S. PATENT DOCUMENTS

| | | | |
|---|---|---|---|
| 3,919,773 | 11/1975 | Freeman | 32/104 |
| 4,192,021 | 3/1980 | Deibig et al. | 623/16 |
| 4,698,375 | 10/1987 | Dorman | 523/115 |
| 5,143,730 | 9/1992 | Fues et al. | 424/426 |

FOREIGN PATENT DOCUMENTS

| | | |
|---|---|---|
| 250994 | 6/1986 | European Pat. Off. . |
| 290983 | 11/1988 | European Pat. Off. . |
| 2620891 | 5/1976 | Fed. Rep. of Germany . |
| 3229540 | 2/1984 | Fed. Rep. of Germany . |
| 3716302 | 5/1987 | Fed. Rep. of Germany . |
| 1-163135 | 6/1989 | Japan . |

*Primary Examiner*—G. S. Kishore
*Attorney, Agent, or Firm*—Ernest G. Szoke; Wayne C. Jaeschke; Daniel S. Ortiz

[57] ABSTRACT

The invention is a resorbable, viscous to solid wax for the mechanical staunching of blood on hard body tissue, particularly bones, based on oligomers of glycolic acid and/or lactic acid and derivatives thereof with monofunctional and/or polyfunctional alcohols and/or corresponding carboxylic acids. The new waxes are characterized by containing body-compatible salts of organic and/or inorganic acids which are formed by corresponding reaction of any free carboxyl groups present in the oligomer wax and/or are incorporated in the wax in homogeneous distribution as added salts.

24 Claims, No Drawings

000# RESORBABLE BONE WAX

This is a continuation of U.S. Ser. No. 07/385,138, filed Jul. 25, 1989 now U.S. Pat. No. 5,143,730.

BACKGROUND OF THE INVENTION

Related Art

Published German patent application P 32 29 540.5 discloses resorbable waxes for the mechanical staunching of blood on hard body tissue, and particularly on bones. The waxes are characterized in that they comprise wax-like polyester oligomers of lower hydroxycarboxylic acids which range from viscous fluids to solids at body temperature. By virtue of their structure, these waxes are degradable by the body's metabolic processes, the degradation rate being adjustable in a known manner. Oligomers of glycolic acid are degraded more quickly by metabolic processes than oligomers of lactic acid. Accordingly, the degradation rate can be regulated, for example, by mixed esterification of the two hydroxycarboxylic acids. The preferred waxes have average molecular weights in the range from about 200 to 1,500 and more preferably in the range from about 300 to 1,000.

According to the published German patent application cited above, monofunctional and/or difunctional alcohols or carboxylic acids or carboxylic anhydrides and/or primary or secondary monoamines may be used to regulate the average molecular weight of the polyester oligomers. A definitive average molecular weight may be determined in advance in known manner by selecting suitable ratios of hydroxycarboxylic acid and the monofunctional or difunctional component. It is known that the reaction products obtained are not uniform in their degree of oligomerization, and contain certain quantities of the starting components.

German patent application P 37 16 302.7 discloses a further optimization of resorbable waxes for the mechanical staunching of blood on hard body tissue. According to this patent application, body-compatible and, in particular, tissue-compatible waxes are obtained when, in accordance with the disclosure of the published German patent application cited above, a certain trifunctional alcohol, namely glycerol, is used to adjust the average molecular weight. The combination of glycerol with oligoesters of lactic acid and/or glycolic acid leads to degradable waxlike components which, on implantation in living body tissue, are distinguished by particularly pronounced compatibility with the body.

Applicants' earlier patent application then discloses that unwanted tissue damage can be avoided particularly safely when through the production process and through subsequent purification of the degradable wax, its content of unreacted carboxyl groups is greatly reduced or is almost completely eliminated. Free carboxyl groups are present in the reaction mixture in the absence of the molecular-weight-regulating dicarboxylic acids proposed in Applicants' above-cited published German patent application. The statistical molecular weight distribution which occurs directly from the production of the waxes always leaves a certain number of free carboxyl groups, which are present at least predominantly as free monomeric hydroxycarboxylic acids, in the oligomeric reaction mixture, even when the desired average number value is adjusted for the molecular weight.

In one particularly preferred embodiment of the invention described in the earlier application, the wax-like material is at least largely freed from its content of unreacted starting components. In particular, the content of unreacted hydroxycarboxylic acids is reduced to residual contents below 0.5% by weight and preferably to residual contents below about 0.2% by weight. In general, the residual contents of unreacted hydroxycarboxylic acids in the waxes will be at or below 0.1% by weight.

The unreacted reactants are said to be preferably removed by a precipitation process in which the desired oligomer fractions are precipitated from a solution or suspension while the unreacted components and/or reaction products of low molecular weight remain in solution.

The problem addressed by the present invention is to further improve resorbable bone waxes in several respects with particular emphasis on the following considerations:

The present invention also seeks to increase the tissue compatibility of the wax implanted in the human or animal body by reducing or substantially eliminating the content of free carboxyl groups in the reaction product. In addition the invention improves the practical handling properties of the waxes to make the work of the surgeon easier. Oligoesters of lactic acid are frequently distinguished by such pronounced viscosity that the wax can be difficult to handle during an operation. The stringing of the oligoester rich in lactic acid, which is particularly useful on physiological grounds, prevents rapid and interference-free handling during the removal of material from the package and during sealing of the bone. Such difficulties arise to only a limited extent, if at all, in the case of oligomeric esters of glycolic acid. For physiological reasons, however, it may be desirable to use waxes based largely on lactic acid. It is known that the degradation of glycolic acid by the body's metabolism takes place by way of oxalic acid. Degradation of lactic acid in the body does not form oxalic acid. If the prevention or restriction of additional oxalic acid formation in the body is indicated, waxes based predominantly on lactic acid will become particularly important for use in operations where a bone wax is used. Accordingly, it is important that the bone wax is easy to handle in practice.

BRIEF SUMMARY OF THE INVENTION

Other than in the operating examples and claims, or where otherwise indicated, all numbers expressing quantities of ingredients or reaction conditions used herein are to be understood as modified in all instances by the term "about".

The invention is based on the observation that high tissue compatibility and improved handling of viscous waxes which, otherwise, are difficult to process may readily be obtained, despite high contents of lactic acid as the basic chemical unit of the polyester molecule, by the introduction of body-compatible carboxylic acid salt groups into the reaction mixture. Instead of removing the unreacted or low molecular weight fractions containing free carboxyl groups from the oligomeric reaction product, the invention proposes neutralizing the free carboxyl groups with suitable bases. It is useful in this regard to introduce additional amounts of body-compatible salts, for example corresponding salts of monomeric hydroxycarboxylic acids, into the wax-like reaction product to reduce the stringing of the reaction products and make them considerably easier to handle.

The present invention provides resorbable, viscous to solid waxes, suitable for the mechanical staunching of blood on hard body tissue, particularly bones, based on oligomers of glycolic acid and/or lactic acid and derivatives thereof with monofunctional and/or polyfunctional alcohols and/or corresponding carboxylic acids. The new waxes are characterized by a content of body-compatible salts of organic and/or inorganic acids which are formed by the corresponding reaction of any free carboxyl groups present in the oligomer wax and/or are homogenously incorporated in the wax as added salts.

DETAILED DESCRIPTION OF THE INVENTION

Suitable bases for forming the carboxylic acid salts include alkali metal oxides or hydroxides, alkaline earth oxides or hydroxides and/or aluminium hydroxide, salts of sodium, calcium and/or magnesium are particularly preferred. The incorporation of salt groups not only affects tissue compatibility and processibility of the bone waxes, in addition valuable biological material can be made available for new bone growth in situ.

In one preferred embodiment of the invention for improving the processibility of the bone wax, salts of glycolic acid and/or lactic acid are added to the bone wax to increase the viscoplastic properties and particularly to reduce the stringing properties of the bone waxes. The stringing properties of waxes based on lactic acid as the polyester-forming molecule can be improved. In this case, the bases mentioned above are preferred as salt-forming cations. It is preferred to limit the content of these added salts of monomeric hydroxycarboxylic acids in the mixture as a whole to approximately 30% by weight. Although higher contents may readily be tolerated in individual cases, it is more preferred to limit the content of such salts to no more than about 20% by weight and, particularly, to no more about 10% by weight. The percentages by weight are based on the oligomer wax.

Instead of or in addition to the above-mentioned salts of organic carboxylic acids and, in particular, the above-mentioned salts of glycolic acid and/or lactic acid, body-compatible salts of inorganic acids may be added to the oligomer components to improve processibility. It has unexpectedly been discovered, that a highly viscous oligomer product based on lactic acid can be converted into a product with far better handling and processing properties simply by the homogeneous incorporation into the bone wax of limited quantities of such inorganic salts in finely divided form. Improved processing properties can be obtained with only small additions of the inorganic salt of less than 10% by weight, based on the weight of the oligomer. However, the addition of larger quantities of inorganic salts can be useful in the practice of the invention. The limiting values mentioned above in regard to the organic salts apply also to the inorganic salt additives.

Particularly useful inorganic salts relate in their chemical constitution to ceramic materials of the type presently being proposed in the literature and in inorganic practice for bone substitutes. The most important class of salts include calcium phosphate ceramic compositions which may be produced in the form of a resorbable material. However, the present embodiment of the invention also encompasses poorly resorbable calcium phosphate ceramic compositions in powder form.

Comparatively readily resorbable calcium phosphates include tricalcium phosphate and its derivatives, which, in exchange for calcium and/or phosphate ions, contain other ions, for example those of fluorine, $=CO_3$ residues, magnesium and the like, in the crystal lattice. This partial replacement of original constituents of the tricalcium phosphate leads not only to changes or disturbances in the lattice structure, but also to differing solubility behavior. For example, solubility increases with the carbonate content but is reduced by the presence of fluorine.

Another inorganic material which is particularly useful in the practice of the invention is hydroxyl apatite or pentacalcium hydroxide triphosphate $Ca_5OH(PO_4)_3$. A powder form hydroxyl apatite can be used in the comparatively readily bioresorbable form initially obtained. However, sintered ceramic materials of this type which are obtained from precipitated calcium phosphate powder at elevated temperature are also useful. Material of this type posseses high stability in biological medium. Literature relating to the use of bioactive materials based on calcium phosphate in the living body is represented, for example, by the following publications: "Resorbierbare keramische Werkstoffe für den Knochenersatz (Resorbable Ceramic Materials as Bone Substitutes)", Biomedizinische Technik, Vol. 20, May 1975, pages 115 et seq; "Neuere Werkstoffe in der medizinischen Technik (Recent Materials in the Medical Field)", Journal "Chemie-Ingenieur-Technik", Number 8, 1975, pages 327 to 333 or DE-PS 22 42 867. The use of particulate calcium sulfate in the outer surface of an implantable plastic part and, hence, ultimately in the living organism is described, for example, in U.S. Pat. No. 3,919,773. Finally, the inorganic salt additions under discussion here in the broader sense also include powdered or ground particles of heterologous bone material, for example corresponding additives which have been prepared from a material corresponding to the so-called "Kieler Knochenspan (Kiel bone chips)". According to U.S. Pat. No. 3,918,100, the growth of natural bone tissue can be stimulated by the use of these ground bone particles, the particles gradually being replaced by new bone growth.

In cases where salts substantially insoluble in wax or corresponding bone solids of the type described above are incorporated in the wax, it is preferred in accordance with the invention to keep the absolute particle size of the individual solid particles below about 250 $\mu$m and more preferably predominantly to particle sizes below about 100 $\mu$m. Not only does the choice of these insoluble solid particles in such finely powdered form ensure homogeneous incorporation, it has also been found that there is no danger in practice of any of the separation processes which can occur with relatively large particles. The mean particle size of these powder-form additives, which are preferably used in accordance with the invention, is below 100 $\mu$m and more preferably in the range from about 1 to 50 $\mu$m.

Preferred waxes according to the invention are produced using glycerol or glycerol partial esters to regulate the average molecular weight of the oligomer fraction, as described for the particularly body and tissue compatible waxes in earlier application P 37 16 302.7. According to the invention, however, the subsequent separation of unreacted reaction products containing free carboxyl groups, as described in the patent application, is replaced by elimination of the free carboxylic acid groups by salt formation with the described bases.

In addition to or instead of glycerol, it is useful to use glycerol partial esters with, in particular, monocarboxylic acids as a partial esterification component. By virtue of their content of free hydroxyl groups, mono and diglycerides of this type regulate the average molecular weight in known manner. At the same time, another component is introduced into the bone wax through the acid moiety present in the partial glyceride and can be used particularly effectively for further influencing the processing properties of the waxes.

Physiologically compatible acids for the formation of the glycerol partial esters are, in particular, relatively long chain fatty carboxylic acids, for example those containing from 8 to 20 and preferably from 12 to 18 carbon atoms. If the desired average molecular weight of the polyester forming components is established, for example, through the couse of tallow fatty acid partial glycerides, the reaction products obtained provide for better handling by spatula.

One particular embodiment of the invention makes use of the following observation: basically viscous and highly stringing oligoester esters based on lactic acid may be substantially improved in their handling properties simply by admixture with relatively small quantities of oligomers of glycolic acid. The glycolic acid oligomers with their greater tendency towards crystallization have an appreciable effect even when mixed with the lactic acid oligomers in quantities of from about 5 to 15% by weight. In this embodiment of the invention, a mixture of oligomers of lactic acid and oligomers of glycolic acid preferably contains at least about 35% by weight and more preferably at least about 50% by weight of lactic acid oligomers. Particularly suitable mixtures contain approximately 75 to 95% by weight lactic acid oligomers and, the rest, glycolic acid oligomers. All of the percentages by weight are based on the particular oligomer mixture used.

In all the described embodiments, i.e. in particular where monomeric salts of lactic acid and/or glycolic acid are used, it can be of advantage in accordance with the invention for the final mixture to contain at least about 35 mol percent and, preferably, at least about 50 mol percent of lactic acid residues, based in each case on the sum of lactic acid and glycolic acid residues in the oligomeric and monomeric state. In particularly useful embodiments, the lactic acid moiety predominates in the mixture so that, for example, at least 60 mol % and preferably at least 75 mol % and up to at least 80 to 90 mol % of the hydroxycarboxylic acid residues are lactic acid residues.

The details of the above-cited DE-OS 32 29 540.5 largely apply to the character and parameters of the waxes. Thus, the polyester oligomers according to the invention are characterized by an average molecular weight of from about 200 to 1,500 and preferably of from about 300 to 1,000. The resorbable waxes are paste-like to soft-spreading materials at body temperature which may be brought into a state in which they spread even more easily by brief heating to temperature of up to about 100° C. and preferably of up to about 60° C. In this form, they are particularly suitable for the mechanical staunching of blood by application as is known per se to body tissue, for example to damaged or otherwise opened bones.

The starting material for the production of the oligomers are the monomeric hydroxycarboxylic acids corresponding to the above definition. However, the easy-to-handle dimerization products, i.e. the lactide and/or the glycolide, may also be used. The lactic acid or the lactic acid dimer may be used as an optically active component, for example L-lactite, or as a mixture of optically active compounds as D,L-lactide.

Preferred waxes according to the invention comprise about 9 to 10 mol of monomeric glycolic acid or about 10 to 12 mol lactic acid, expressed as monomeric hydroxycarboxylic acid, per mol of glycerol. The method of preparing the oligomers useful in the present invention is disclosed in the above-cited DE-OS 32 29 540.

The salt formation, with the free carboxyl groups in the reaction mixture, may be carried out with the corresponding free bases and/or with suitable salts of those bases. Particularly suitable salts are, for example, the carbonates and/or bicarbonates.

Although additional purification processes may be carried out, for example by recrystallization of the reaction mixture, they are not generally necessary.

In another embodiment of the invention, other known bone waxes based on oligomers of glycolic acid and/or lactic acid or derivatives thereof with monofunctional and/or polyfunctional alcohols and/or corresponding carboxylic acids are mixed with the bone waxes of the invention. Particularly useful bone waxes of this type are mixtures with alkaline earth salts of higher fatty acids, particularly those containing from about 12 to 18 carbon atoms. Corresponding calcium salts, particularly calcium palmitate and/or calcium stearate, can advantageously be used as such mixture components. The quantity in which these components are used is preferably no more than about 50% by weight, based on the wax as whole, and more preferably not more than about 35% by weight. Homogeneous mixtures may readily be formed by mixing the components in a common melt.

The embodiments of the invention also require that any salts used be physiologically compatible inorganic and/or organic salts of the type described above. As in the above-described embodiments of the invention, the co-use of the salts in the present embodiment, additionally provides for the advantageous incorporation of other growth factors for accelerated bone regeneration and new bone growth in the composition. In this connection, reference is made for example to the Article by W. Krüger et al. in "Dtsch. zahnärztl. Z." 43, 709 to 712 (1988), which describes the effect of using hydroxyl apatite and growth-promoting mitogenic protein adsorbed thereon in inducing bone regeneration in animal experiments.

EXAMPLES

In the following Examples, four oligomer waxes based on glycolic acid/glycerol (A, B) and on lactide/-glycerol (C, D) were used as basic materials for the particular series of tests.

The following investigations are carried out:
1) neutralization of the free acid groups with equivalent quantities of calcium carbonate;
2) mixing of the resins with calcium glycolate or with calcium lactate;
3) addition of hydroxyl apatite to the resins;
4) addition of limited quantities of the neutralized resin B based on glycolic acid to the neutralized resin C based on lactic acid.

The neutralization of the free acid groups and the additions are carried out in a melt at 100° C. with stirring. The content of free acid (glycolic acid/lactic acid) of the bone waxes described was determined by titration. The free acid was then neutralized by addition of an equivalent quantity of $CaCO_3$ and intensive mixing.

A description of the materials, the mixed products and the tests used for evaluation are as follows:

1. Tests and materials a. Appearance: visual evaluation b. Viscosity measurement Measurement of the cone/plate viscosity using the following instrument: EIC VISCO-Plot, a product of Epprecht Instruments and Controls AG/Switzerland, REL cone/plate; the measurements were carried out using the D measuring element at 20 r.p.m./100° C. (setting 1).

Stringing

The samples of material to be tested are poured into an aluminium dish and tested after cooling for 24 hours:

c. Determination of stringing

A metal spatula (width 9 mm) is pressed vertically into the wax layer and slowly pulled upwards after penetrating to a depth of 3 mm. The string length at break is measured in cm.

d. Hydroxyl apatite powder
Penta-calcium hydroxytriphosphate
$Ca_5(PO_4)_3(OH)$
Merck/Darmstadt
Particle size 2 to 100 μm e. Ca glycolate/Ca lactate DL lactic acid (racemate) or glycolic acid is dissolved in three times the quantity of water, heated to approximately 70° C. in a water bath and neutralized with an equivalent quantity of $CaCO_3$ by addition in portions. The water is then completely removed in a rotary evaporator at 80° to 90° C./10 mbar.

The coarse-grained material obtained was size-reduced without powder emission in a mixer (Braun).

2. Production and description of the resorbable starting waxes a. Waxes produced from glycolic acid/glycerol General procedure for the preparation of the reaction products of glycolic acid with glycerol Glycolic acid and glycerol were introduced into a three-necked flask equipped with a stirrer and a distillation head and heated to 150° C. under nitrogen and the reaction continued for 3 to 5 hours until no more water of reaction was recovered. The flask was then carefully evacuated to 10 torr at 150° C. After another 2 hours under these reaction conditions, the contents of the flask were cooled to 100° C., the vacuum was eliminated, the product was neutralized as described above and decanted while still hot.

The composition of the mixtures and the oligomer properties are shown in Table 1.

TABLE 1

| | Oligohydroxycarboxylic Acids of Glycolic Acid and Glycerol | | | | | |
|---|---|---|---|---|---|---|
| | Educts | | Yield water | Consistency | VISCOSITY | |
| Example | Glycolic acid mol | Glycerol mol | of reaction Percent | at Room Temperature | 100° C. MK-D at 20 r.p.m. | Stringing (cm at break) |
| A | 8 | 1 | 100 | cloudy, highly viscous | 5,000 mPa · s | 2 |
| | | after neutralization | | cloudy, highly viscous | 5,000 mPa · s | 7 |
| B | 9 | 1 | 99.1 | cloudy, highly viscous | 10,000 mPa · s | 2 |
| | | after neutralization | | cloudy, highly viscous | 10,000 mPa · s | 7 | b. Waxes produced from lactide and glycerol

General procedure for the preparation of the reaction products of lactide with glycerol Lactide (L(−)-Lactid N, a product of Böhringer Ingelheim) and glycerol were introduced under nitrogen into a conventional laboratory apparatus and heated over a period of 1 hour with stirring to a temperature of 195° C. The mixture was then left to react for 3 hours at 195° C. and decanted after neutralization. An Sn(II) chloride solution in ether was added as catalyst (7 ml of a solution of 2.5 g $SnCl_2$ in 1000 ml ether in the reaction of 3 mol lactide with 1 mol glycerol).

The composition and the oligomer properties are shown in Table 2.

TABLE 2

| | Oligohydroxy Carboxylic Acids of Glycerol and Lactide | | | | |
|---|---|---|---|---|---|
| | Educts | | Consistency at Room | VISCOSITY 100° C. | Stringing |
| Examples | Glycerol mol | Lactide mol | Temperature | MK-D at 20 r.p.m. | (cm at break) |
| C | 1 | 5 | clear, viscous | 8,000 mPa · s | approx. 60 |
| | | after neutralization | cloudy, highly viscous | 10,000 mPa · s | 30 |
| D | 1 | 6 | clear, viscous | 10,000 mPa · s | approx. 50 |
| | | after neutralization | cloudy, highly viscous | 10,000 mPa · s | 30 |

3. Process for filling the bone waxes and properties of the mixtures

The melts of the neutralized bone waxes were filled with the following substances while stirring at temperatures of 100° to 120° C.:

a. Ca glycolate (2.5–20%)
b. Ca lactate (2.5–20%)
c. hydroxyl apatite (2.5–20%)

Filling was followed by intensive mixing for 15 minutes. After cooling (storage for 24 hours in an aluminium dish), consistency, stringing and the cone/plate viscosity at 100° C. were evaluated.

The results are shown in Tables 3 to 12.

TABLE 3

| Bone Wax | Addition of Ca glycolate (% by weight) | Consistency at Room Temperature | VISCOSITY 100° C. MK-D at 20 r.p.m. | Stringing (cm at break) |
|---|---|---|---|---|
| A | 2.5 | wax-like | 25,000 | no stringing |

TABLE 3-continued mPa · s

TABLE 4

| Bone Wax | Addition of Hydroxyl Apatite | Consistency at Room Temperature | VISCOSITY 100° C. MK-D at 20 r.p.m. | Stringing (cm at break) |
|---|---|---|---|---|
| A | 2.5 | wax-like | 25,000 mPa · s | no stringing |
|   | 5.0 | wax-like | 41,000 mPa · s | no stringing |
|   | 7.5 | wax-like | 61,000 mPa · s | no stringing |

TABLE 5

| Bone Wax | Addition of Ca Glycolate (% by weight) | Consistency at Room Temperature | VISCOSITY 100° C. MK-D at 20 r.p.m. | Stringing (cm at break) |
|---|---|---|---|---|
| B | 2.5 | wax-like | 61,000 mPa · s | longer than 1 cm |
|   | 5 | wax-like | 66,000 mPa · s | no stringing |
|   | 7.5 | wax-like, gritty, partly crystalline | 71,000 mPa · s | no stringing |
|   | 10 | wax-like, gritty, partly crystalline | 76,000 mPa · s | no stringing |
|   | 12.5 | wax-like, gritty | 92,000 mPa · s | no stringing |
|   | 15 | wax-like, gritty | 97,000 mPa · s | no stringing |
|   | 17.5 | wax-like, gritty, dry | 102,000 mPa · s | no stringing |
|   | 20 | wax-like, gritty, dry | 112,000 mPa · s | no stringing |

TABLE 6

| Bone Wax | Addition of Ca Lactate (% by weight) | Consistency at Room Temperature | VISCOSITY 100° C. MK-D at 20 r.p.m. | Stringing (cm at break) |
|---|---|---|---|---|
| B | 2.5 | cloudy, highly viscous | 87,000 mPa · s | approx. 1 |
|   | 5 | cloudy, highly viscous | 92,000 mPa · s | approx. 1 |
|   | 7.5 | wax-like | 102,000 mPa · s | no stringing wax-like |
|   | 10 | wax-like | 115,000 mPa · s |   |
|   | 12.5 | wax-like, gritty | 122,000 m · Pas |   |
|   | 15 | wax-like, gritty | 125,000 mPa · s |   |
|   | 17.5 | wax-like, gritty | 128,000 mPa · s |   |
|   | 20 | wax-like, gritty | 133,000 mPa · s |   |

TABLE 7

| Bone Wax | Addition of Ca Glycolate (% by weight) | Consistency at Room Temperature | VISCOSITY 100° C. MK-D at 20 r.p.m. | Stringing (cm at break) |
|---|---|---|---|---|
| C | 2.5 | cloudy, highly viscous | 10,000 mPa · s | 12 |
|   | 5 | cloudy, highly viscous | 10,000 mPa · s | 10 |
|   | 7.5 | cloudy, highly viscous | 20,000 mPa · s | 6 |
|   | 10 | cloudy, highly viscous | 30,000 mPa · s | 5 |
|   | 12.5 | cloudy, partly crystalline | 41,000 mPa · s | 4 |
|   | 15 | cloudy, partly crystalline | 51,000 mPa · s | 4 |
|   | 17.5 | cloudy, wax-like, partly crystalline | 66,000 mPa · s | 3 |
|   | 20 | cloudy, wax-like | 76,000 mPa · s | 3 |

TABLE 8

| Bone Wax | Addition of Ca Lactate (% by weight) | Consistency at Room Temperature | VISCOSITY 100° C. MK-D at 20 r.p.m. | Stringing (cm at break) |
|---|---|---|---|---|
| C | 2.5 | cloudy, highly viscous | 10,000 mPa · s | 12 |
|   | 5 | cloudy, highly viscous | 15,000 mPa · s | 8 |
|   | 7.5 | cloudy, highly viscous | 30,000 mPa · s | 6 |
|   | 10 | cloudy, highly viscous | 40,000 mPa · s | 5 |
|   | 12.5 | cloudy, partly crystalline | 61,000 mPa · s | 3 |
|   | 15 | cloudy, partly crystalline | 71,000 mPa · s | 2 |
|   | 17.5 | cloudy, partly crystalline | 92,000 mPa · s | approx. 2 |
|   | 20 | cloudy, wax-like | 107,000 mPa · s | approx. 2 |

TABLE 9

| Bone Wax | Addition of Hydroxyl Apatite Powder (% by weight) | Consistency at Room Temperature | VISCOSITY 100° C. MK-D at 20 r.p.m. | Stringing (cm at break) |
|---|---|---|---|---|
| C | 5 | cloudy, highly viscous | 15,000 mPa · s | 7 |
|  | 7.5 | cloudy, highly viscous | 22,000 mPa · s | 6 |
|  | 10 | cloudy, highly viscous | 39,000 mPa · s | 5 |
|  | 15 | cloudy, highly viscous | 61,000 mPa · s | 3 |

TABLE 10

| Bone Wax | Addition of Ca Lactate (% by weight) | Consistency at Room Temperature | VISCOSITY 100° C. MK-D at 20 r.p.m. | Stringing (cm at break) |
|---|---|---|---|---|
| D | 12.5 | cloudy, partly crystalline | 67,000 mPa · s | no stringing |

TABLE 11

| Bone Wax | Addition of Hydroxyl Apatite Powder (% by weight) | Consistency at Room Temperature | VISCOSITY 100° C. MK-D at 20 r.p.m. | Stringing (cm at break) |
|---|---|---|---|---|
| D | 5 | cloudy, highly viscous | 39,000 mPa · s | 5 |
|  | 7.5 | cloudy, highly viscous | 61,000 mPa · s | 3 |
|  | 10 | cloudy, highly viscous | 67,000 mPa · s | 3 |
|  | 15 | cloudy, highly viscous | 78,000 mPa · s | 1 |
|  | 20 | highly viscous, wax-like | 90,000 mPa · s | no stringing |

In a following series of tests, quantities of 5, 10 and 20% by weight neutralized bone wax B were added to the neutralized bone wax C. The values of the respective mixed products are shown in Table 12.

TABLE 12

| Addition of Bone Wax B % by weight | Consistency at Room Temperature | VISCOSITY 100° C. MK-D at 20 r.p.m. | Stringing (cm at break) |
|---|---|---|---|
| 5 | Cloudy, highly viscous | 10,000 mPa · s | 27 |
| 10 | highly viscous, partly crystalline | 20,500 mPa · s | 20 |
| 20 | highly viscous, partly crystallized | 41,000 mPa · s | 17 |

We claim:

1. A resorbable, body compatible viscous to solid wax for the mechanical staunching of blood on hard body tissue, comprising: at least one oligomer composition formed by the esterification of at least one acid selected from the group consisting of glycolic acid and lactic acid or such oligomers chain-terminated with at least one composition selected from the group consisting of monohydroxyl alcohols, polyhydroxyl alcohols and the corresponding carboxylic acids; and at least one body-compatible salt of an organic or an inorganic acid homogeneously distributed in the wax, the at least one oligomer composition being neutralized with a body-compatible salt forming composition.

2. A resorbable wax of claim 1, containing a body compatable salt of an organic acid formed in situ by reaction of free carboxyl groups of an organic acid present in the wax with a body compatable salt forming composition.

3. A resorbable wax of claim 1 containing a body compatible salt which is mixed with the wax.

4. Resorbable waxes of claim 1, containing at least one carboxylic acid salt of a metal selected from the group consisting of alkali metal, alkaline earth metal and aluminium.

5. A resorbable wax of claim 4 wherein the metal is selected from the group consisting of sodium, calcium and magnesium.

6. A resorbable wax of claim 1 containing not more than about 30% by weight of the oligomer of at least one composition selected from the group consisting of salts of glycolic acid, salts of lactic acid, salts of inorganic acids and body-compatible ceramic materials.

7. A resorbable wax of claim 6 containing not more than about 10% by weight of the at least one composition.

8. A resorbable wax of claim 1 containing a calcium phosphate.

9. A resorbable wax of claim 8 wherein the calcium phosphate is hydroxy apatite.

10. A resorbable wax of claim 1 containing salts, substantially insoluble in the wax, having a maximum particle size of up to about 250 μm.

11. A resorbable wax of claim 10 wherein the salts have a particle size of less than about 100 μm.

12. A resorbable wax of claim 10 wherein the salts have a mean particle size of from about 1 to about 50 μm.

13. A resorbable wax of claim 1 wherein the oligomer components are chain terminated by reaction with at least one compound selected from the group consisting of glycerol and glycerol partial esters with fatty acids.

14. A wax of claim 1 wherein the at least one oligomer composition is neutralized to a content of unreacted carboxylic acid below about 0.5% by weight of the oligomer.

15. A way of claim 14 wherein the content of unreacted carboxylic acid is less than about 0.2% by weight of the oligomer composition.

16. A wax of claim 14 wherein the content of unreacted carboxylic acid is less than about 0.1% by weight of the oligomer composition.

17. A composition of claim 13 wherein free carboxyl groups are neudtralized with body compatible salt forming alkaline compounds.

18. A composition of claim 17 wherein the content of free carboxylic acid is less than about 0.5% by weight of the composition.

19. A composition of claim 18 wherein the content of free carboxylic acid is less than about 0.2% by weight of the composition.

20. A composition of claim 19 wherein the content of free carboxylic acid is less than about 0.1% by weight of the composition.

21. A resorbable wax of claim 1 which is pasty to soft-spreading at body temperature.

22. A resorbable wax of claim 1 which can be made pasty by heating to a temperature below about 100° C.

23. A resorbable wax of claim 1 wherein the polyester oligomers have an average molecular weight in the range from about 200 to about 1,500.

24. A resorbable wax of claim 23 wherein the polyester oligomers have an average molecular weight in the range of from about 300 to about 1000.

* * * * *